(12) United States Patent
Takiguchi et al.

(10) Patent No.: US 7,402,381 B2
(45) Date of Patent: Jul. 22, 2008

(54) METHOD OF IMMOBILIZING MOLECULES ONTO A SOLID PHASE SUBSTRATE AND METHOD OF FABRICATING A BIOSENSOR USING THE METHOD

(75) Inventors: Hiroshi Takiguchi, Suwa (JP); Hitoshi Fukushima, Suwa (JP)

(73) Assignee: Seiko Epson Corporation, Tokyo (JP)

( * ) Notice: Subject to any disclaimer, the term of this patent is extended or adjusted under 35 U.S.C. 154(b) by 90 days.

(21) Appl. No.: 10/927,073

(22) Filed: Aug. 27, 2004

(65) Prior Publication Data
US 2005/0079528 A1   Apr. 14, 2005

(30) Foreign Application Priority Data
Sep. 11, 2003   (JP)   ............... 2003-319815

(51) Int. Cl.
*G01N 33/543* (2006.01)
(52) U.S. Cl. .......................... 435/4; 310/311; 310/312; 310/313 R; 310/340; 422/50; 422/57; 422/68.1; 422/82.01; 422/82.02; 422/82.11; 435/6; 435/7.1; 435/174; 435/175; 435/176; 435/177; 435/180; 435/181; 435/182; 435/287.1; 435/287.2; 435/287.9; 436/518; 436/524; 436/525; 436/526; 436/527; 436/528; 436/529; 436/530; 436/531; 436/532
(58) Field of Classification Search .............. 435/4, 435/6, 7.1, 174–177, 180–182, 287.1, 287.2, 435/287.9; 422/50, 57, 68.1, 82.11, 82.01–82.02; 436/518, 86, 524–532; 310/311, 312, 313 R, 310/340
See application file for complete search history.

(56) References Cited

U.S. PATENT DOCUMENTS 5,532,128 A * 7/1996 Eggers et al. ............... 435/6
5,804,047 A * 9/1998 Karube et al. .......... 204/403.04
6,159,681 A * 12/2000 Zebala ......................... 435/4
6,241,863 B1 * 6/2001 Monbouquette .......... 205/777.5
6,281,004 B1 * 8/2001 Bogen et al. ............. 435/287.1
2002/0168640 A1 * 11/2002 Li et al. ....................... 435/6
2003/0119014 A1 * 6/2003 Donner et al. ................. 435/6

FOREIGN PATENT DOCUMENTS

| JP | A 05-203608 | 8/1993 |
|---|---|---|
| JP | A 06-009699 | 1/1994 |
| JP | A 07-048449 | 2/1995 |
| JP | A 07-072059 | 3/1995 |
| JP | A 2001-200050 | 7/2001 |
| JP | A 2001-303022 | 10/2001 |
| JP | A 2003-075448 | 3/2003 |
| JP | A 2003-194820 | 7/2003 |
| JP | A 2003-248001 | 9/2003 |
| JP | A 2005-504294 | 2/2005 |
| WO | WO 03/027679 A1 | 4/2003 |

* cited by examiner

*Primary Examiner*—Christopher L Chin
(74) *Attorney, Agent, or Firm*—Oliff & Berridge, PLC

(57) ABSTRACT

Aspects of the invention can provide a method capable of easily realizing immobilization with the optimum density derived from a concentration control and without phase separation in coadsorption of a number of molecules. The immobilization method can include the step of dissolving a plurality of molecules to be immobilized to a solid phase substrate with a solvent to obtain a solution of the plurality of molecules, and the step of incubating the solution and the solid phase substrate in touch therewith. Each of the molecules can include a solid phase substrate joint portion having a jointing property to the solid phase substrate, a functional portion having a specific function, and a linker portion positioned between the solid phase substrate joint portion and the functional portion.

23 Claims, 3 Drawing Sheets

METHOD OF IMMOBILIZING MOLECULES ONTO A SOLID PHASE SUBSTRATE AND METHOD OF FABRICATING A BIOSENSOR USING THE METHOD

BACKGROUND OF THE INVENTION

1. Field of Invention

Aspects of the invention relate to a method of immobilizing molecules onto a solid phase substrate, especially to method of immobilizing a plurality of molecules to a single substrate, a method of fabricating a biosensor using the molecule immobilization method, and method of detecting a target material.

2. Description of Related Art

Related biosensors with molecules having affinity with target materials and fixed on solid phase substrates are becoming in widely spread use for detecting the target materials included in test samples. These related biosensors utilize mutual interactions (hybridizations) between complementary nucleic acid strands, enzymes and stromas, enzymes and coenzymes, antigens and antibodies, or other mutual interactions between accepters and their ligands to capture target materials on surfaces of solid phase substrates, thereby determining directly or indirectly (e.g., determination using fluorescent molecules combined with the target materials) presence of the target materials. Therefore, the probes are often biomolecules, such as nucleic acids, proteins, or sugars.

Methods of immobilizing these biomolecules onto substrates are categorized mainly into methods (e.g., nucleic acid elongation reaction) of composing these molecules directly on solid phase substrates and methods of immobilizing previously composed molecules to surfaces of substrates. As an example of the latter methods, a method can be used in which a specific group is coupled, via a linker, to the tail end of a molecule to be immobilized and the molecule is absorbed onto a solid phase substrate by incubating a solution including the molecule with contacting to the substrate. The absorption method is particularly used in case of immobilizing a molecule difficult to be composed on a substrate or when immobilizing a number of kinds of different molecules onto a single substrate.

In immobilizing probe molecules by the absorption method, if the pitch of the probes is too narrow, relatively large, bulky target molecules, such as DNA or proteins, may interfere each other with coupling with the probe. Accordingly, in the absorption method, in order to control the density of the probes so that as many probe molecules and target molecules as possible are effectively be coupled, relatively small molecules called spacer is generally added to the probe molecule solution to be immobilized simultaneously.

Meanwhile, as a related biosensor which immobilizes enzymes as probes and utilizes specificity of enzyme-stroma reactions, for instance, a sensor which immobilizes glucose oxidases to measure glucoses in a test sample is known and is under development also as a blood sugar level measuring instrument for home use. Although in glucose sensors, electrode activation materials, such as oxygen or hydrogen peroxide, are generally monitored by electrodes around the time of mutual interactions between glucoses and glucose oxidases, since an amount of dissolved oxygen is not sufficient in case of blood as a test sample. A related method using an electronic mediator, which is a charge transfer complex functioning substitute for oxygen can be used. See, for example, Japanese Unexamined Patent Publication No. 5-203608. Accordingly, in glucose sensors, if both of glucose oxidases and electronic mediator molecules are immobilized in a single solid phase substrate, glucoses can effectively be detected.

In order to immobilize on a single substrate a number of kinds of molecules, such as nucleic acid molecules and spacer molecules or enzymes and enzyme mediators, a coabsorption method can be used. In the coabsorption method, a solid phase substrate can be dipped in a solution containing mixture of a number of kinds of molecules and an amount of molecules absorbed to the solid phase substrate is adjusted by altering the mixing ratio of the molecules, thus enabling, in theory, a density of immobilized probe in the biosensor to be controlled only by initially adjusting the composing ratio of the mixed solution. In view of application to diagnosis or safety tests of foods, biosensors capable of detecting a number of materials included in a test sample at a time are required, and the coabsorption method is hoped to be a technology capable of immobilizing a number of kinds of probe molecules to a solid phase substrate at a time.

SUMMARY OF THE INVENTION

Combinations, such as nucleic acid molecules and spacer molecules or enzymes and enzyme mediators, have large differences in molecular weights. Generally, since small molecules are absorbed to solid phase substrates faster than polymers, for example, in coabsorption of nucleic acid molecules and spacer molecules of small molecules, the spacer molecules are absorbed by far faster and thus covering a majority of the surface of the substrate. In order to immobilize nucleic acid molecules with the optimum density, the both must be mixed with a great difference in concentration, which is difficult to be controlled. Further, some combinations of coabsorption do not form a uniform mixture on a solid phase substrate but causes phase separation, which cannot achieve the optimum density even if the concentrations are controlled. Aspects of the invention can solve the problems described above to provide an effective and distinguished method of immobilizing a number of molecules with densities optimum thereto in a coabsorption process.

In immobilizing a number of molecules on a solid phase substrate, by making each of the molecules include a common structure derived from polyethylene glycols or the like to make properties as whole molecules such as hydrophilicity or solubility similar to each other, the difference in absorption speeds can be reduced, and accordingly, even if there is a significant difference in molecular weights or characteristics of portions to function as probes or spacers, a uniform mixed film can be formed, and the ratio of compounds to be immobilized can easily be controlled by controlling the concentration ratio of the respective compounds.

Aspects of the invention relate to an immobilization method that can include the step of dissolving a plurality of molecules to be immobilized to a solid phase substrate with a solvent to obtain a solution of the plurality of molecules, and the step of incubating the solution and the solid phase substrate in touch therewith. Each of the molecules can include a solid phase substrate joint portion having a joining property to the solid phase substrate, a functional portion having a specific function, and a linker portion positioned between the solid phase substrate joint portion and the functional portion. In the method, the linker portion can be derived from a compound selected from a group consisting of polyethylene glycol, polypeptide, sugar, polyester, polyisocyanate, carbamic ester, and polyurethane. The solid phase substrate joint portion can be a functional group capable of forming a self-assembled monomolecular film comprising the molecules.

The plurality of molecules can include a molecule having the functional portion composed of one of nucleic acid and protein. The plurality of molecules can include a molecule having the functional portion composed of enzyme and enzyme mediator. The plurality of molecules can include a molecule having the functional portion composed of at least one of a functional group and a compound, the functional group being selected from a group consisting of hydroxyl group, amino group, ferrocenyl group, and carboxyl group, the compound being selected from a group consisting of benzoquinone, N-methylphenazium, and biotin. Additionally, the immobilization method can include a total concentration of the plurality of molecules in the solution that is in a range from 0.3 to 5 µM.

A method of fabricating a biosensor including the immobilization method can include a biosensor including a molecule composed mainly of a solid phase substrate joint portion, a functional portion, and a linker portion positioned between the solid phase substrate joint portion and the functional portion, the molecule being joined to a solid phase substrate via the solid phase substrate joint portion. The biosensor can be the solid phase substrate is made of one of glass, polymer resin, carbon, metal, semiconductor, and metal oxide.

A method of detecting a target material in a test sample using the biosensor can include incubating the biosensor and the test sample in touch therewith using a gold deposited substrate as the solid phase substrate, the gold deposited substrate being made by depositing gold thin film on a surface of a glass substrate, irradiating a light beam, one of continuously and intermittently around incubating step, to the solid phase substrate of the biosensor from the surface opposite to the surface having the molecule immobilized thereto, and measuring an alteration in the angle (resonance angle) with which the strength of reflected light corresponding to the light inputted thereto in step irradiating is reduced. A method of detecting a target material in a test sample using the biosensor can include incubating the biosensor and the test sample in touch therewith using a gold electrode of a crystal oscillator as the solid phase substrate, measuring an alteration in frequency of the crystal oscillator, one of continuously and intermittently around incubating step.

A plurality of molecules to be immobilized to a solid phase substrate used in the invention can include a solid phase substrate joint portion, a functional portion, and a linker portion positioned between the both portions. The plurality of molecules can be a number of molecules of the same kind or a number of kinds of molecules. The invention is particularly suitable in case a number of kinds of molecules are required to be immobilized.

In the invention, a solid phase substrate joint portion can have a joining property to the solid phase substrate and is preferably composed of a functional group capable of forming a high density and high orientation self-assembled monomolecular film (Self-Assembled Monolayer, SAM) on a surface of the solid phase substrate. The functional group is selected in accordance with a kind of the solid phase substrate, and it is known that, for example, thiol group, disulfide group, or sulfide group is used for gold surface of the solid phase substrate and siloxy group is used for glass substrate to preferably form the SAM film. However, it should be understood that the invention is not limited to these combinations.

In the invention, a functional portion can denote a portion necessary for making the surface of the solid phase substrate having a plurality of molecules immobilized thereto using the immobilization method according to the present invention function as a biosensor. Accordingly, the functional portion can be derived from a probe compound having a specific affinity with a target material to be detected using the biosensor, a spacer functional group disposed between the probe compounds so that the probe compounds are immobilized with a reasonable density, a mediator used, when the probe compound is an enzyme, to help the activity of the enzyme, and so forth.

In the invention, a linker portion positioned between the solid phase joint portion and the functional portion can be derived from a compound selected from a group consisting of polyethylene glycol, polypeptide, sugar, polyester, polyisocyanate, carbamic ester, and polyurethane. According to presence of the linker portion, hydrophilicity, solubility, and molecular weight become similar, and an uniform mixed film having good dispersibility can be formed. As long as such an effect is provided, the whole of plurality of molecules included in a single solution can comprise the same kind of linker portion, or can comprise different linker portion from each other. Further, the linker portion can be formed by directly linking the compound described above with the solid phase substrate joint portion and the functional portion respectively, or can be formed by linking the compound with the solid phase substrate joint portion and the functional portion via other functional groups or the like attached to the compound described above.

In the invention, nucleic acid used as the functional portion can be partially or fully modified (substituted) and denotes oligonucleotide or polynucleotide respectively having a single-strand or a double-strand, and preferably a single-strand oligonucleotide or polynucleotide which can partially or fully be modified (including substitution). As a preferable example of the nucleic acid, a nucleic acid selected from DNA, RNA, PNA (peptide nucleic acid), CNA (cyclohexylethanoic acid nucleic acid), HNA (hexitol nucleic acid), p-RNA (pyranosil RNA), oligonucleotide comprising the nucleic acid molecules, and polynucleotide comprising the nucleic acid molecules can be cited. If nucleic acid is used as the functional portion, those skilled in the art can easily link the linker portion to its 3' end or 5' end using a method known to the public. The biosensor having nucleic acid immobilized thereto as a probe can be used for detection of target nucleic acid molecule, sequence analysis, gene mapping, and so on.

In the invention protein used as a functional portion denotes at least two amino acids bonded by covalent bond and includes a group of protein, polypeptide, oligopeptide, and peptide. The protein can be formed of natural amino acids and peptide bonding or synthetic peptide pseudo structure. Those skilled in the art are able to link protein to the linker portion using a method known to the public, and to utilize, for example, a chemical reaction of amino group with succinate or carboxyl group (e.g., Japanese Unexamined Patent Publication No. 6-9699), or a specific absorption reaction between protein and stroma. If polyethylene glycol (PEG) is used as the linker portion, the ω end of PEG is modified with an acetal group and is linked to an amino group of the protein using a reduced amination reaction (e.g., Japanese Unexamined Patent Publication No. 2001-200050.) If direct linkage of the protein and the linker portion is difficult, it is possible to link them with proper molecules bound therebetween. Biotin can be cited as an example of such molecules.

By immobilizing protein onto the surface of the solid phase substrate, it can be used as a biosensor for capturing a target material utilizing enzyme-stroma reactions, antigen-antibody reactions, or other acceptor-ligand reactions, or the like.

The biomolecules used as the functional portions are not limited to nucleic acid or protein, but various sugars or glycoprotein or the like can also be used.

According to the immobilization method of the invention, a molecule having the functional portion composed of an enzyme and a molecule formed of the mediator of the enzyme can be immobilized on a single substrate by a coabsorption process. By coabsorbing the both, the activity of the enzyme can sufficiently be brought out. As such a mediator molecule, for example, a group of ferrocene, benzoquinone, N-methylphenazium, or other enzymes (e.g., horseradish peroxidase, etc.) can be used.

Further, as the functional portion, functional groups, such as hydroxyl group, amino group, ferrocenyl group, and carboxyl group, can be used as well. These functional groups can be used as the spacer molecules to optimize the immobilization density of the probe molecules such as nucleic acid or protein, or can also be used as probes to capture target molecules.

In the invention, the molecules to be immobilized to the solid phase substrate include salts of the molecules. Salt used in the invention have no particular limitations and any type of salt can be included provided it can form a salt with the compound to be immobilized. More specifically, addition salts of inorganic acids (e.g., hydrochloride, hydrosulfate, carbonate, bicarbonate, hydrobromate, hydriodate, etc.); addition salts of organic carboxylic acids (e.g., acetate, maleate, lactate, tartrate, trifluoroacetate, etc.); addition salts of organic sulfonic acids (e.g., methanesulfonate, hydroxymethanesulfonate, hydroxyethanesulfonate, benzenesulfonate, toluenesulfonate, taurinate, etc.); addition salts of amine (e.g., trimethylamine salt, triethylamine salt, N,N'-dibenzylethylenediamine salt, N-methylglucamine salt, diethanolamine salt, triethanolamine salt, tris(hydroxyamino)methane salt, phenethylbenzylamine salt, etc.); and addition salts of amino acids (e.g., arginine salt, lysine salt, serine salt, glycine salt, aspartate, glutamate, etc.) and so forth can be used.

A plurality of molecules including the functional portion, the linker portion, and the solid phase substrate joint portion is mixed prior to be provided for the absorption reaction with the surface of the solid phase substrate, and then used as the solution. In the solution used in the present invention, the plurality of molecules is included with a typical total concentration of 0.1 μM through 20 μM, and if the concentration is within this range, the cover of the solid phase substrate with the molecules can be completed in a good condition. A more preferable range of the total concentration is from 0.1 μM to 10 μM, and a further preferable range is 0.3 μM through 5 μM. In the composition, it should be understood that the composing ratio (mole %) of the compounds or their salts to be immobilized is not limited, but can be selected by those skilled in the art in accordance with a probe density, a probe structure, a spacer molecule in use or its structure, nature of the solid phase substrate in use, and so on.

A method of preparing the solution, in which the plurality of molecules is dissolved, is not limited, but any solvents and any mixing processes can be used providing it can dissolve the molecules and does not disturb the absorption reaction. The plural molecules can sequentially be dissolved in a single solution, or plural solutions can be prepared for respective molecules and then mixed. For example, if the total concentration of the probe molecule and the spacer molecule in the solution need to be X μM (X is within a range of 0.1 through 20), the probe molecule solution and the spacer molecule solution are individually prepared with concentrations of X μM, and then mixed with each other in a desired mixing ratio, thus obtaining the objective mixed solution of X μM. As a solvent suitable for use with the functional portion comprising a biomolecule, various kinds of phosphoric acid buffer solution (e.g., PBS (50 mM $KPO_4$, 1M NaCl, pH 7.0) or the like), TE buffer solution (mixed buffer solution of tris-HCl and EDTA, pH 8.0), or the like can be cited. The buffer solution is not limited in its pH, but typically has nearly pH 5.5 through 8.5, and more preferably about pH 7 through 8.

In the immobilization method according to the invention, the reaction temperature, in incubating the mixed solution containing the compound to be immobilized with the solid phase substrate in touch therewith, is not particularly limited, but typically 0 through 40 degree centigrade, and preferably 20 through 35 degree centigrade. The reaction time is not limited, but typically 30 minutes through 24 hours of incubating is sufficient, and it is preferably 1 hour to 12 hours.

The invention also provides a fabrication method of a biosensor including the use of the above immobilization method, and the definitions described above are applied to various conditions used in the fabrication method in the same way.

Further, the invention can also provide a biosensor comprising a molecule composed mainly of a solid phase substrate joint portion, a functional portion, and a linker portion positioned between the solid phase substrate joint portion and the functional portion, the molecule being joined to a solid phase substrate via the solid phase substrate joint portion. The definitions described above are also applied to the terms used in the biosensor in the same way.

Solid phase substrate used in the invention is not limited and any solid phase substrates can be used therefor as long as the functional group of the solid phase substrate joint portion preferably form the SAM film on its surface. The best conditions for materials or thickness of the solid phase substrate can be selected by those skilled in the art dependently on the nature of the solid phase substrate joint potion, a signal detection means used for detecting a target molecule, and so on. As examples preferable for the material of the substrate, a glass substrate, a metal substrate (e.g., gold, silver, cupper, aluminum, platinum, alumina, $SrTiO_3$, $LaAlO_3$, $NdGaO_3$, $ZrO_2$, etc.), a silicon substrate (e.g., silicon dioxide), a polymer resin substrate (e.g., polyethylene terephthalate, polycarbonate), carbon (graphite), and so on can be cited.

The solid phase substrate used in the invention can be composed of a single material included in the materials listed above, or of a substrate (a first substrate) of one material and a film (a first layer) of at least one of other materials formed on the substrate, or, in addition, at least one interfacial layers (a second layer, a third layer, etc.) formed between the first substrate and the first layer. As specific examples preferable for solid phase substrate, the glass substrate having a glass substrate as the first substrate and a metal film (preferably a gold thin film, a silver thin film, a cupper thin film, or a platinum thin film) formed on the surface thereof as the first layer can be cited. Note that the interfacial layer made of an other material can be provided between the glass substrate and the metal film.

The metal layers including the first layer can be formed by a process known to the public or a process similar thereto. They can be formed by, for example, an electric gilding process, an electroless plating process, a sputter process, a deposition process, an ion plating process, or the like. Then any contamination is removed from the surface of the metal film by rinsing out with an organic solvent, and further, as required, by decomposition with a strong acid or ozone generated by ultraviolet lays.

Although the thickness of solid phase substrate used in the invention is not particularly limited, in case of the first substrate described above, it is typically in a range of about 0.1 through 30 mm, and preferably in a range of about 0.1 through 2 mm.

Detection method according to the invention denotes a method in which a target material or its related material included in a test sample is captured using the biosensor according to the invention to determine presence or absence of the target material. As a method of determining presence or absence of an interaction between probe molecule immobilized on the surface of the biosensor and the target material, a method using a fluorescent molecule or a radioactive material as a marker, a surface plasmon resonance (SPR) method, a quartz crystal microbalance (QCM) method, a method of detecting by a mass alteration without using the marker molecules, and so on can be cited.

In the SPR method, a test sample is analyzed using a phenomenon that, when a light beam is inputted from the opposite surface of a solid phase substrate to the surface, on which the compounds are immobilized, with an angle greater than the critical angle, an angle (resonance angle), with which the reflected light beam corresponding to the inputted light beam is weakened, alters in accordance with the mass alteration of the material linked on the surface of the solid phase substrate. Specifically, if the target material is linked with the probe immobilized on the surface of the solid phase substrate, the alteration of mass (increase of mass) occurs, thus the resonance angle is increased. In using the SPR method, the solid phase substrate is preferably made of a transparent material such as glass, polymeric resin, or plastics, and a gold thin film is preferably formed on the surface on which the compounds are immobilized.

In the QCM method, a phenomenon that the resonance frequency of a quartz crystal oscillator is decreased in accordance with the mass of the material absorbed on the surface of the electrode of the quartz crystal oscillator is utilized, and the probe molecules are immobilized on the surface of the electrode to detect the interaction between the probe molecules and the target material. Accordingly, in using the QCM method, the probes are preferably immobilized on the electrode surface of the quartz crystal oscillator using the immobilizing method according to the present invention.

If the interaction between the probe molecules and the target material is detected by previously marking the target material, optically or electrochemically detectable molecules, for example, fluorescent molecules such as FITC (fluorescein isotheocyanate), RITC (rhodamine isothiocyanate), or the like, or the quantum dots can be used. If the probe molecules and the target material are both nucleic acids, it can be marked by adding the intercalator after the interaction.

According to the invention, a method of immobilizing a plurality of molecules on a shingle solid phase substrate with the optimum density and arrangement can be provided. According to the immobilization method of the invention, a number of different kinds of molecules can be uniformly immobilized without any phase separations in only one process, and only by controlling the concentration of each compound, a biosensor having functional portions arranged in the optimum density can easily be fabricated. By using this biosensor, a number of target materials can be detected simultaneously form a test sample. And further, a biosensor suitable for the interaction between a probe and a target material requiring a mediator can be provided.

BRIEF DESCRIPTION OF THE DRAWINGS

The invention will be described with reference to the accompanying drawings, wherein like numerals reference like elements, and wherein.

DETAILED DESCRIPTION OF PREFERRED EMBODIMENTS

Reference examples, exemplary embodiments, and examination examples regarding the invention are described below only for exemplification, and it should be understood that the invention is not limited to the exemplary embodiments described below. Those skilled in the art can fully put the invention into practice with various modifications added to the exemplary embodiments described herein, the modifications being included in the scope of the claims as attached.

Molecules for immobilization having functional portions having a hydroxyl group, DNA, or a biotin can be obtained. Structures of the respective molecules are described below.

(A) SH—$(C_2H_4O)_7$—OH (hereinafter referred to as molecule (A)) (B) SH—$(CH_2)_6$—$(C_2H_4O)_6$-DNA (hereinafter referred to as molecule (B))

(C) SH—$C_2H_4$—CONH—$(C_2H_4O)_9$-biotin (hereinafter referred to as molecule (C))

Thiol group (SH—) corresponds to a solid phase substrate joint portion, polyethylene glycol —$(C_2H_4O)_7$— in the compound (A), —$(CH_2)_6$—$(C_2H_4O)_6$—in the compound (B), and —$C_2H_4$—CONH—$(C_2H_4O)_9$— in the compound (C) correspond to linker portions, and a hydroxyl group (—OH), DNA, and the biotin respectively correspond to functional portions.

Subsequently, PBS (50 mM $KPO_4$, 1M NaCl, pH 7.0) can be prepared as a solvent, and the molecules (A), (B), and (C) are mixed with a ratio of 60:20:20 (mole %) to have a total concentration of 0.5 μM.

As a solid phase substrate, a gold electrode of a quartz oscillator prepared according to the fabrication method described above can be used. The gold electrode is dipped in the solution obtained in the dissolution process, and incubated for about 20 minutes.

Figure 1:
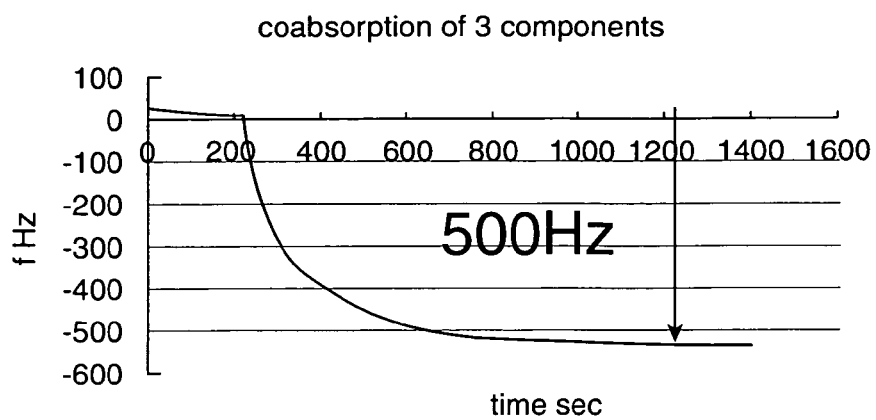
FIG. 1 is a graphical chart of a QCM measurement result showing coabsorption of molecules (A) through (C)

FIG. 1 shows a result of measuring the process by QCM method. A frequency alteration of about 500 Hz is observed, and it is confirmed that a mass alteration (an absorption reaction) has occurred on the surface of the electrode.

Figure 6:
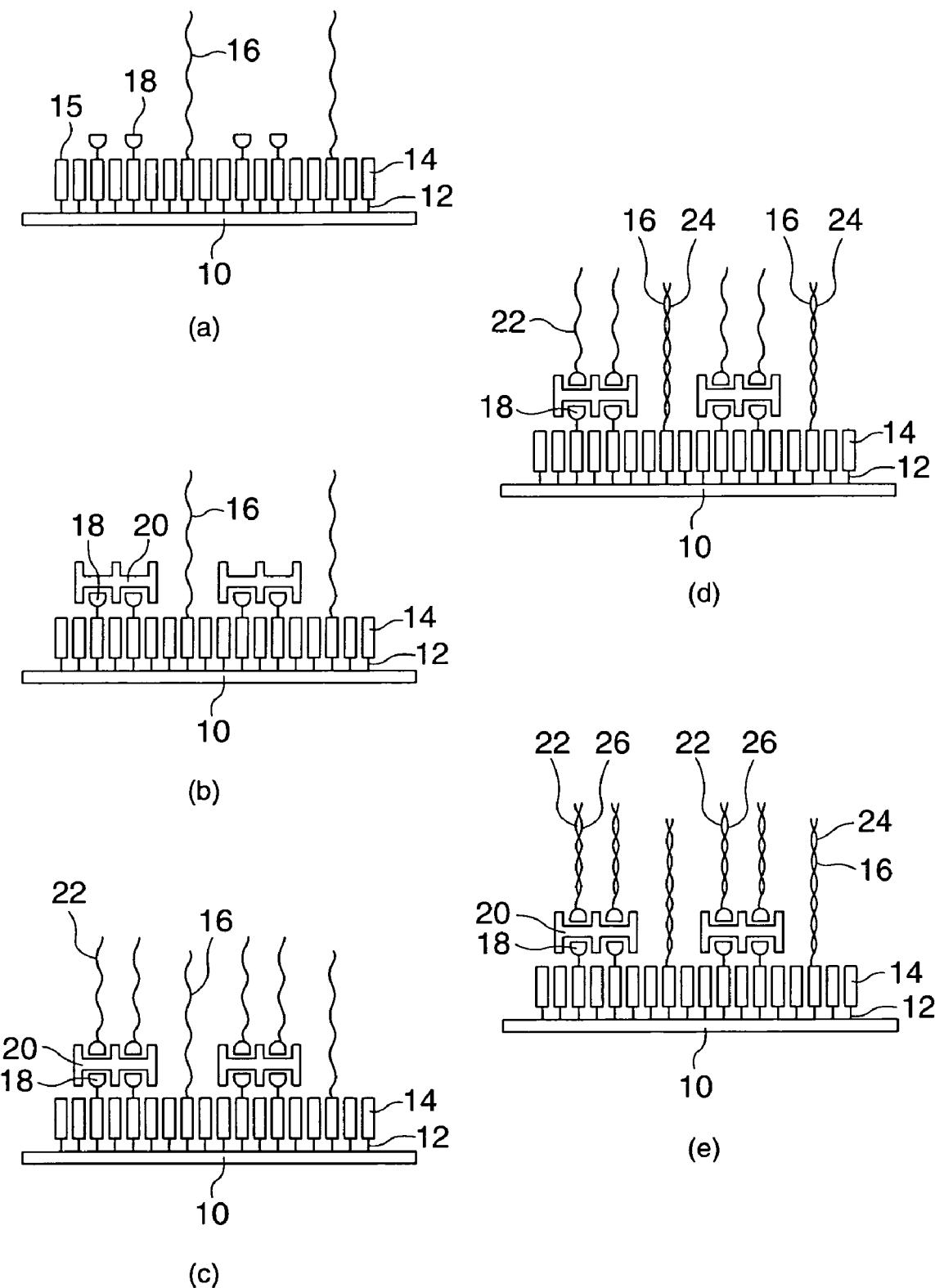
FIGS. 6($a$), 6($b$), 6($c$), 6($d$), and 6($e$) are schematic views showing processes of respective experiments of absorption or hybridization.

As confirmed by a verification experiment described below, in the present process, the molecules (A), (B), and (C) are absorbed on the surface of the electrode. The condition is schematically shown in FIG. 6($a$). The linker portion 14 is linked to the surface of the electrode 10 via the thiol group 12 which is the solid phase substrate joint portion, and the molecule (B) 16 having the DNA linked to the linker portion 14, the molecule (C) 18 having the biotin linked thereto, and the molecule (A) having the hydroxyl group linked thereto are immobilized in an uniformly mixed manner without the phase separation.

Then, a proper quantity of water solution of streptavidin (concentration of 1 g/L), which is protein linkable with biotin, is added to the PBS ($KPO_4$, NaCl) buffer solution in which the substrate with the molecules (a) through (C) immobilized thereto is dipped, and the incubation is executed for 15 minutes.

Figure 2:
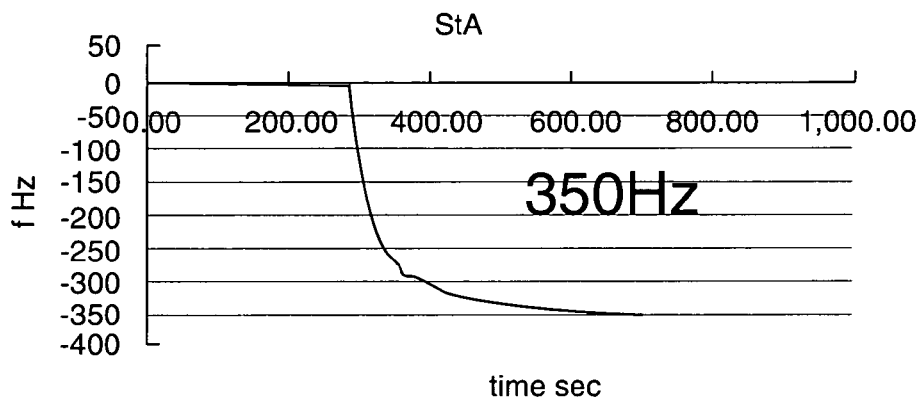
FIG. 2 is a graphical chart of a QCM measurement result showing absorption of streptavidin.

FIG. 2 shows a result of measuring the process by QCM method. A frequency alteration of about 350 Hz is observed, and it is confirmed that an absorption reaction has occurred. The density of the absorbed molecules is found out to be $2.51 \times 10^{12}$ molecules/cm$^2$ by calculation. It is confirmed form this result that the molecule (C) has been absorbed on the surface of the electrode during the incubation process.

The result of the present verification experiment is schematically shown in FIG. 6(b). The biotin portions of the molecules (C) immobilized with reasonable spaces are linked with linking sites of streptavidin 20.

The biosensor obtained above can be reacted with DNA (dA20) linked with biotin in the PBS (50 mM KPO$_4$, 1M NaCl) solution and the incubation is executed for 15 minutes.

Figure 3:
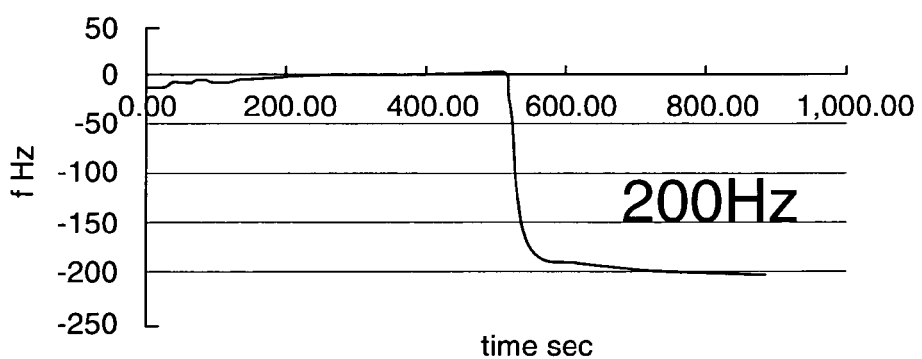
FIG. 3 is a graphical chart of a QCM measurement result showing absorption of biotin labeled DNA.

FIG. 3 shows a result of measuring the process by QCM method. A frequency alteration of about 200 Hz is observed, and it is confirmed that an absorption reaction has occurred on the surface of the solid phase substrate. The density of the absorbed molecules is found out to be $7.0 \times 10^{12}$ molecules/cm$^2$ by calculation. Since this density is higher than the density of the molecules linked in the verification experiment-1, it is confirmed that the biotin labeled DNA and streptavidin are linked in a ratio more than 1:1, and activity of each of four biotin linking sites of streptavidin has not been lost.

The result of the present verification experiment is schematically shown in FIG. 6(c). The biotin portion of the biotin labeled DNA 22 is linked with the linking site of streptavidin 20 where no biotin is linked in the verification experiment-1.

Nucleic acid having a base sequence (29 bases) completely complementally with the nucleic acid included in the molecule (B) is added to the biosensor obtained above, and then the incubation is executed for about one hour.

Figure 4:
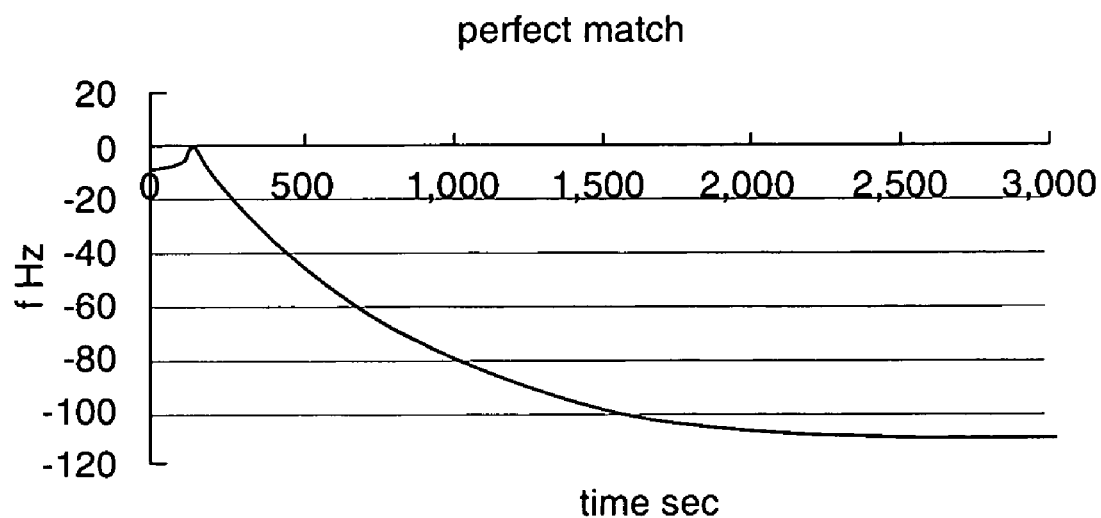
FIG. 4 is a graphical chart of a QCM measurement result showing hybridization of molecules (B)

FIG. 4 shows a result of measuring the process by QCM method. As a result, an alteration in frequency of 110 Hz has been observed, and thus the hybridization of the molecule (B) with the nucleic acid with 29 bases has been confirmed. The nucleic acid hybridized with the molecule (B) is found out to be $4.46 \times 10^{12}$ molecules/cm$^2$ by calculation. It is confirmed form this result that the molecule (B) has been absorbed on the surface of the electrode during the incubation process.

The result of the present verification experiment is schematically shown in FIG. 6(d). The nucleic acid 24 with 29 bases is hybridized with the DNA portion of the molecule (B) 16 absorbed in the incubation process.

Nucleic acid having a base sequence (20 bases) complementally with the biotin labeled DNA used in the verification experiment-2 is added to the biosensor obtained above, and then the incubation process is executed for about ten minutes.

Figure 5:
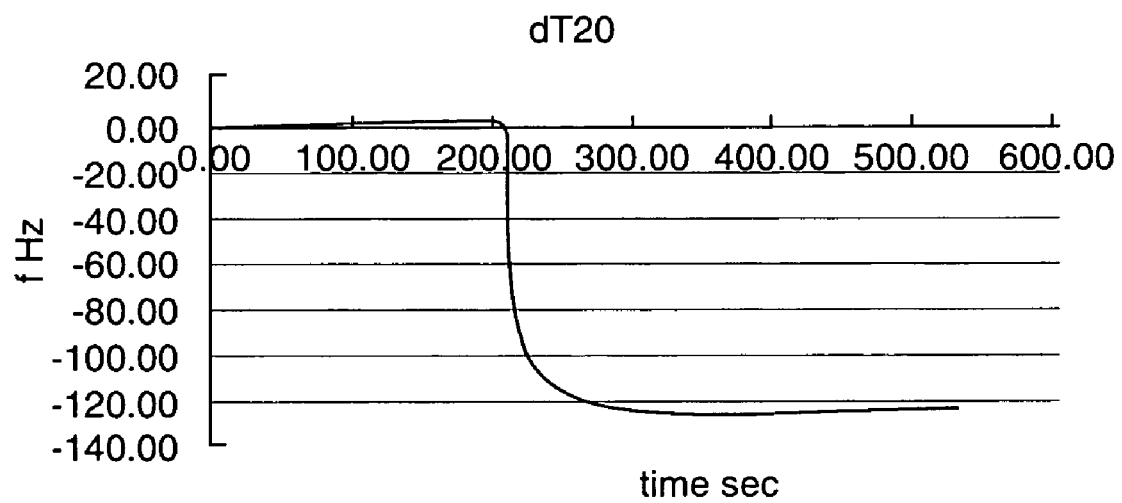
FIG. 5 is a graphical chart of a QCM measurement result showing hybridization of biotin labeled DNA.

FIG. 5 shows a result of measuring the process by QCM method. As a result, an alteration in frequency of 120 Hz has been observed, and thus the hybridization of the biotin labeled DNA with the nucleic acid with 20 bases has been confirmed. The nucleic acid hybridized with the biotin labeled DNA is found out to be $7.69 \times 10^{12}$ molecules/cm$^2$ by calculation. From these results, it has been confirmed that the biotin labeled DNA is linked with streptavidin in the verification experiment-2 with the DNA portion maintaining its linking ability.

The result of the present verification experiment is schematically shown in FIG. 6(e). The nucleic acid 24 with 20 bases is hybridized with the DNA portion of the biotin labeled DNA 22.

Although, in the verification experiment described above, an experiment for directly confirming the absorption of the molecule (A), in view of the fact that the hydroxyl group has very small molecular weight in comparison to the nucleic acid or the biotin and the molecule (A) has the highest mixture ratio, it is obvious that the molecule (A) has been absorbed prior to other molecules.

Note that although the verification experiments 1 through 4 are executed to show that the molecules (A) through (C) have preferably been absorbed, the experiments shows at the same time that the solid phase substrate, to which the molecules (A) through (C) are immobilized by the immobilization method according to the present invention, can be used as a biosensor.

In other words, it has been proven by the verification experiments described above that, with the molecule (A) immobilized, the nucleic acid having a base sequence complementally with the DNA of the molecule (A) can be detected, and with the molecule (B) immobilized, streptavidin can be detected. Although, in the present verification experiments, these matters are detected by QCM method, they can be detected as well by SPR method, an electrochemical measurement method, or a method using marker molecules such as fluorescence molecules.

From the above, it has been confirmed that a biosensor having both DNA and protein immobilized in suitable densities for maintaining respective linking functions can be fabricated by a immobilization method according to the invention.

While this invention has been described in conjunction with the specific embodiments thereof, it is evident that many alternatives, modifications, and variations will be apparent to those skilled in the art. Accordingly, preferred embodiments of the invention as set forth herein are intended to be illustrative, not limiting. There are changes that may be made without departing from the spirit and scope of the invention.

What is claimed is:

1. A method of immobilization, comprising:
   immobilizing a plurality of first molecules and a plurality of second molecules to a solid phase substrate by putting a solution of the plurality of first and second molecules in contact with the solid phase substrate,
   each of the plurality of first molecules having a first functional portion that is used for recognizing a first object to be examined,
   each of the plurality of first molecules including a first joint portion, the first functional portion being immobilized through the first joint portion that is capable of binding to the solid phase substrate,
   each of the plurality of second molecules having a second functional portion that is different from the first functional portion and that functions as a mediator of the first functional portion, and
   each of the plurality of second molecules including a second joint portion, the second functional portion being immobilized through the second joint portion that is capable of binding to the solid phase substrate.

2. The method according to claim 1,
   the plurality of first molecules and the plurality of second molecules constituting a self-assembled monomolecular film.

3. The method according to claim 1,
   the first functional portion including an enzyme or an enzyme mediator.

4. The method according to claim 1,
   the first functional portion including a hydroxyl group, an amino group, a ferrocenyl group, and a carboxyl group.

5. The method according to claim 1,
a total concentration of the plurality of first molecules and the plurality of second molecules being in a range from 0.3 to 5 μM.

6. A method of fabricating a biosensor including the immobilization method according to claim 1.

7. The method according to claim 1,
positioning a first linker portion in each of the plurality of first molecules so as to be connected between the first functional portion and the solid phase substrate, and
positioning a second linker portion in each of the plurality of second molecules so as to be connected between the second functional portion and the solid phase substrate.

8. The method according to claim 7,
the first linker portion being one group selected from polyethylene glycol, polypeptide, sugar, polyester, polyisocyanate, carbamic ester, and polyurethane.

9. The method according to claim 1,
the second functional portion being used for recognizing a second object that is to be examined and that is different from the first object.

10. The method according to claim 9,
the second functional portion hybridizing the second object.

11. The method according to claim 1,
the first joint portion being identical with the second joint portion.

12. The method according to claim 1,
the first functional portion hybridizing the first object.

13. The method according to claim 1,
the solid phase substrate functioning as an electrode.

14. A biosensor, comprising:
a substrate;
a plurality of first molecules that are immobilized to the substrate, each of the plurality of first molecules having a first functional portion that is used for recognizing a first object to be examined, and each of the plurality of first molecules including a first joint portion, the first functional portion being immobilized through the first joint portion that is capable of binding to the substrate; and
a plurality of second molecules that are immobilized to the substrate, each of the plurality of second molecules having a second functional portion that is different from the first functional portion and that functions as a mediator of the first functional portion, and each of the plurality of second molecules including a second joint portion, the second functional portion being immobilized through the second joint portion that is capable of binding to the substrate.

15. The biosensor according to claim 14,
the substrate being made of one of glass, polymer resin, carbon, metal, semiconductor, and metal oxide.

16. A method of detecting a target material in a test sample using the biosensor according to claim 14, comprising:
incubating the biosensor and the test sample in contact therewith using a gold deposited substrate as the solid phase substrate, the gold deposited substrate being made by depositing gold thin film on a surface of a glass substrate;
irradiating a light beam, continuously or intermittently, around the incubating step, to the solid phase substrate of the bio sensor from a surface opposite to a surface having the molecule immobilized thereto;
measuring an alterration in an angle (resonance angle) with which a strength of reflected light corresponding to the light inputted thereto in the irradiating step is reduced; and
determining whether a target is detected based on the measurement of the alteration in the angle.

17. A method of detecting a target material in a test sample using the biosensor according to claim 14, comprising:
incubating the biosensor and the test sample in contact therewith using a gold electrode of a crystal oscillator as the solid phase substrate;
measuring an alteration in frequency of the crystal oscillator, continuously or intermittently, around the incubating step; and
determining whether a target is detected based on the measurement of the alteration in the frequency.

18. The biosensor according to claim 14,
the second functional portion being used for recognizing a second object that is to be examined and that is different from the first object.

19. The biosensor according to claim 18,
the second functional portion capable of hybridizing the second object.

20. The biosensor according to claim 14,
the first joint portion being identical with the second joint portion.

21. The biosensor according to claim 14,
the first functional portion capable of hybridizing the first object.

22. The biosensor according to claim 14,
the substrate functioning as an electrode.

23. A method of immobilization, comprising:
immobilizing a plurality of first molecules and a plurality of second molecules to a solid phase substrate by putting a solution of the plurality of first and second molecules in contact with the solid phase substrate,
each of the plurality of first molecules having a first functional portion that is used for recognizing a first object to be examined,
each of the plurality of first molecules including a first joint portion, the first functional portion being immobilized through the first joint portion that is capable of binding to the solid phase substrate,
each of the plurality of second molecules having a second functional portion that is different from the first functional portion,
each of the plurality of second molecules including a second joint portion, the second functional portion being immobilized through the second joint portion that is capable of binding to the solid phase substrate, and
the plurality of first molecules and the plurality of second molecules constituting a self-assembled monomolecular film.

* * * * *